United States Patent
Scholz

Patent Number: 6,136,036
Date of Patent: *Oct. 24, 2000

[54] ENDOPROSTHESIS FOR AN ARTIFICIAL HIP-JOINT

[76] Inventor: Werner Scholz, Alte Döhrener Strasse 76, 30173 Hannover, Germany

[*] Notice: This patent is subject to a terminal disclaimer.

[21] Appl. No.: 09/144,070

[22] Filed: Aug. 31, 1998

Related U.S. Application Data

[63] Continuation of application No. 08/806,432, Feb. 26, 1997, Pat. No. 5,800,554.

[30] Foreign Application Priority Data

Feb. 29, 1996 [DE] Germany .................... 196 07 609
May 24, 1996 [DE] Germany .................... 296 09 287 U

[51] Int. Cl.$^7$ .................... A61F 2/36; A61F 2/32
[52] U.S. Cl. .................... 623/23.11; 623/22
[58] Field of Search .................... 623/22, 22.11, 623/23.11, 22.12–0.19, 23.12–0.27

[56] References Cited

U.S. PATENT DOCUMENTS

| | | |
|---|---|---|
| 3,102,536 | 9/1963 | Rose et al. . |
| 3,864,758 | 2/1975 | Yakich . |
| 4,502,160 | 3/1985 | Moore et al. . |
| 4,892,546 | 1/1990 | Kotz et al. . |
| 5,071,435 | 12/1991 | Fuchs et al. . |
| 5,358,524 | 10/1994 | Richelsoph . |
| 5,569,263 | 10/1996 | Hein . |
| 5,800,554 | 9/1998 | Scholz . |

FOREIGN PATENT DOCUMENTS

| | | |
|---|---|---|
| 0 121 491 A1 | 10/1984 | European Pat. Off. . |
| 0 474 015 A1 | 3/1992 | European Pat. Off. . |
| 0 610 575 A2 | 8/1994 | European Pat. Off. . |
| 0 621 019 A1 | 10/1994 | European Pat. Off. . |
| 2310120A | 5/1975 | France . |
| 2 349 319 | 4/1976 | France . |
| 2606628A | 11/1986 | France . |
| 2689756 | 10/1993 | France . |
| 3605 630 A1 | 9/1987 | Germany . |
| 3935 488 A1 | 5/1991 | Germany . |
| 4445892 A1 | 6/1996 | Germany . |
| 29609287 U1 | 10/1996 | Germany . |
| 660 955 | 6/1997 | Switzerland . |

OTHER PUBLICATIONS

European Search Report EP 96 11 8430, 2pp.
OSTEO AG, Endoprothesen System nach Prof Mittelmeier (1980).

*Primary Examiner*—Mickey Yu
*Assistant Examiner*—Alvin Stewart
*Attorney, Agent, or Firm*—Shlesinger Arkwright & Garvey LLP

[57] ABSTRACT

The present invention concerns an endoprosthesis for an artificial hip-joint, the endoprosthesis including a shank (1) having an adapter (2) at one of its ends. A ballhead (4) is fitted with a recess (6) detachably engaged by the adapter (2) while retaining the ballhead. The adapter (2) and the recess (6) are cylindrical, whereby the ballhead (4) is axially adjustable. A device is provided for retaining the ballhead (4) in various axial positions relative to the adapter (2). Accordingly, the ballhead (4) is adjustable with respect to its axial position and thereby its distance from the adapter (2) or the shank (1) is likewise adjustable. This feature eliminates the need to stock different ballheads matching different anatomic particulars.

9 Claims, 2 Drawing Sheets

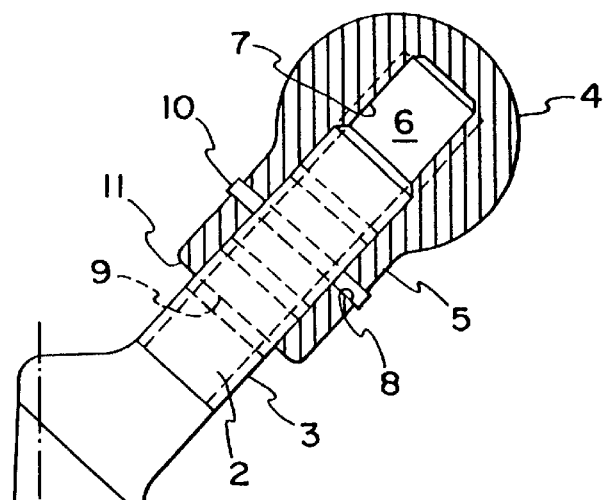
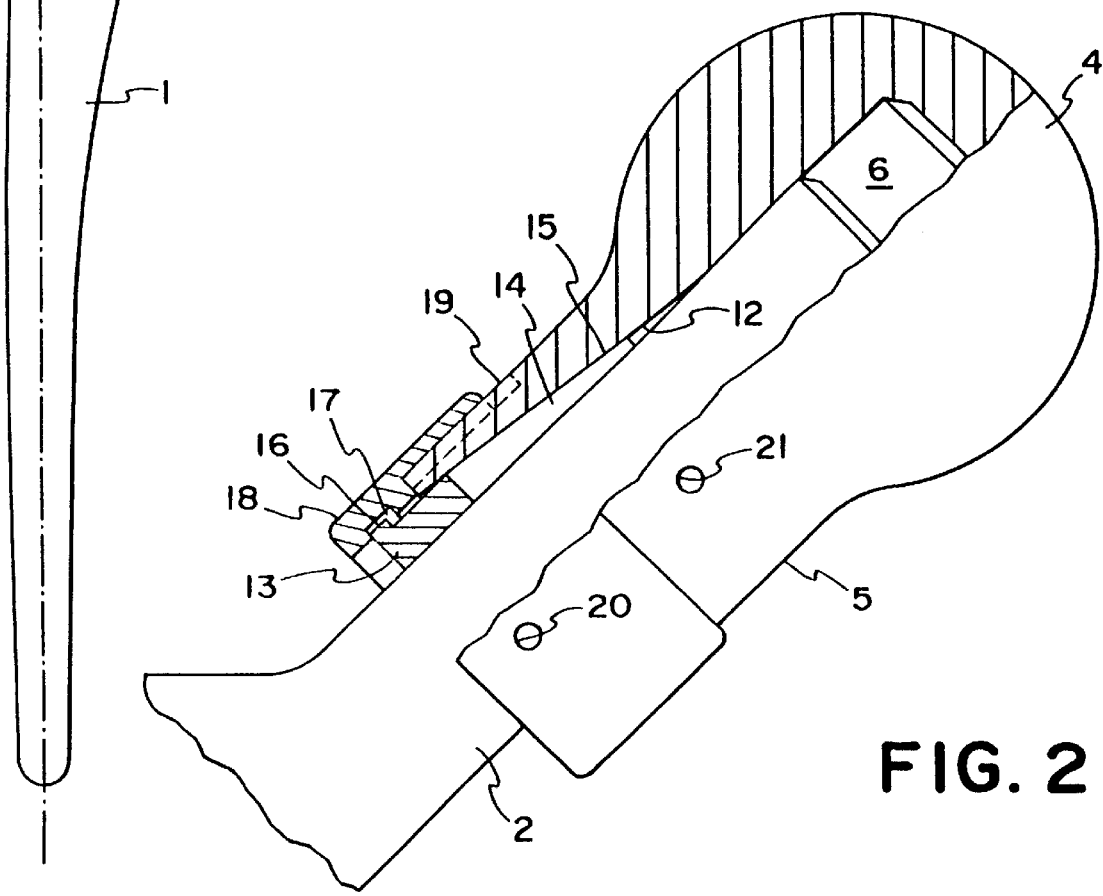

ENDOPROSTHESIS FOR AN ARTIFICIAL HIP-JOINT

This application is a continuation of U.S. Ser. No. 08/806,432 filed Feb. 26, 1997 now U.S. Pat. No. 5,800,554.

FIELD OF THE INVENTION

The present invention relates to prosthetic devices and in particular an endoprosthesis for an artificial hip-joint.

BACKGROUND OF THE INVENTION

A prior art endoprosthesis is shown in a publication entitled "*Endoprothesen-System nach Prof. Mittelmeier*" issued by OSTEO AG of Selzach, Switzerland. This endoprosthesis comprises a shank insertable essentially over its full length into a patients thighbone and evincing a conical adapter at its free end to receive a ballhead with a matching conical recess. Ballheads of different configurations may be affixed to the conical adaptor. In particular, the various ballheads evince different outside diameters with the conical recesses shown mounted at different axial distances relative to the ballhead. The above assembly permits matching of the ballhead position to the adapter and hence to the shank and the thighbone.

The above endoprosthesis system incurs the drawback whereby several ballheads having different locations of the conical recess relative to the center of the ballhead must be stocked in order to be able to match the ballhead position relative to the adapter and hence the shank, depending upon the particular needs of the patient. Stocking of ballheads is cumbersome as well as costly. Moreover matching of the ballheads is only roughly possible if ballhead stocking is kept within bounds.

OBJECTS AND SUMMARY OF THE INVENTION

It is therefore an object of the present invention to provide an endoprosthesis that permits matching of the ballhead position to the shank without the need for a large inventory of stocked ballheads having different-sized affixing recesses.

The basic concept of the present invention is the removal of the connection between ballhead and the shank or the adapter in the form of a self-locking conical connection, and instead to design the adapter and recess in the ballhead to be essentially cylindrical, whereby interconnection between ballhead and the adapter or the shank is feasible in various axial positions.

In an additional feature of the present invention, nothing further is required thereupon or to achieve a desired axial position of the device other than merely mounting of the fastening system. Accordingly, the predominant forces from the ballhead are transmitted by cylindrical seizure onto the adapter with the means affixing the ballhead in various axial positions relative to the adapter being of many varied designs.

One way of affixation may be in the form of fitting the ballhead with an inside thread and the adapter with an outside thread. As a result, the ballhead is easily threaded onto the adapter, with the axial position of the ballhead relative to the adapter or shank being adjusted or changed by means of the depth of threading. This threaded connection transmits all predominant forces, also in the axial direction, the only additional requirement being to secure the particular threaded-in position by suitable means, for instance using a locknut. However, permanent fastening might only result with sufficient seizure of the threads or by using highly-viscous means or adhesives spanning the threads. But such features would entail difficulties if subsequently the ballhead should have to be unscrewed for exchange.

An appropriate design within the present invention for the means for securing a given threaded-in position is the provision of at least two cross-boreholes within the ballhead or in an extension of the ballhead, and running in the direction of the cylindrical recess and inside the adapter, the cross-boreholes being aligned with one another in various threaded-in positions and in a manner such that a securing pin can be pressed in or screwed in. The securing pin being required only to secure the threaded-in position, it is hardly affected by stresses and as a result, high reliability against undesired loosening is achieved.

In an appropriate development of the above embodiment, the distance of the cross-borehole in the ballhead or extension from the front edge of the cylindrical recess corresponds to the spacing between the cross-boreholes in the adapter or a multiple thereof. With this design, when the front edge, as seen in direction of screwing, of the cylindrical recess is aligned with a cross-borehole in the adapter, a threaded-in position is obtained thereby wherein the cross-borehole in the ballhead or the extension also is aligned with a cross-borehole in the adapter. As a result, such alignment is easily noticed, and time consuming trial-and-error is no longer needed to find that position for which the securing pin can be threaded-in or pressfitted-in.

In another embodiment of the present invention, the ballhead together with its cylindrical recess is axially displaceable on the adapter and the means affixing the ballhead at different axial positions relative to the adapter are clamping means. In this embodiment, the ballhead is continuously adjustable relative to the adapter and more precise matching to the anatomic requirements of the patient is possible when implanting the artificial hip joint.

The clamping means required for ballhead displaceability may be designed in a number of ways within the scope of the present invention. In one embodiment, the clamping means is in the form of a clamping sleeve of the type conventionally used in lathes to hold round materials.

In another development of the present invention, the clamping means comprises a clamping sleeve having a cylindrical inside surface that allows for displacement on the adapter; one end of the clamping sleeve is fitted with a conically tapering outer surface entering a complementary portion of the ballhead recess, the other clamping-sleeve end rests against a nut screwed onto the ballhead. By tightening of the nut, the clamping sleeve is forced by its conical portion into the complementary conical recess in the ballhead and thereby the ensuing wedging assures wholly reliable clamping.

If the seat of the clamping sleeve on the cylindrical adapter is designed to allow slight displaceability, then, when tightening, the conical clamping-sleeve portion must be compressed, entailing a fairly substantial force additional to that required for tightening of the nut. To avoid applying such additional force, a further embodiment of the present invention provides that the clamping sleeve be axially slitted at least in the region of the conically tapering outer surface. As a result, the clamping sleeve is able to tightly hug the cylindrical adapter without the need for additional application of force as the nut is being tightened, and the conical clamping-sleeve end will be forcefully wedged into the conically complementary portion of the ballhead recess.

Appropriately, the nut is a coupling nut screwed onto an extension of the ballhead. In an especially appropriate manner, the coupling nut of the present invention is geometrically linked in both axial directions with the clamping sleeve. In other words, the clamping sleeve will follow every threading motion of the axial displacement of the coupling nut so that the sleeve is not only forced inward during nut tightening, but furthermore, when the coupling nut is being loosened, the sleeve also will be pulled out of its wedged position. This feature is especially advantageous during "testing"; that is, when trying to find the most anatomically advantageous position for the patient. Tightening and subsequent loosening of the present invention is easily carried out in any adjusted position.

Obviously, screwing implements must be applied to tighten the nut, and at the same time the ballhead or an extension of it should be able to seat screwing implements. Flats may be provided for that purpose. However, in an especially advantageous embodiment, a borehole and preferably a blind hole to receive a pin wrench is provided at the outside of the coupling nut and/or in the outside of the ballhead extension.

In order to also apply the present invention to the above described prior art hip-joint endoprostheses which are fitted with a conical adapter at the shank end intended to receive a ballhead with a complementary conical recess, a further embodiment of the present invention provides that the adapter be a separate component and comprise a recess at its end facing the shank, where the latter recess is conically complementary to a conical adapter mounted at the shank end, and in such a manner that the adapter can be mounted in a self-locking manner onto the conical adapter. As a result, a separately designed adapter can be mounted on the conical adapter of a known shank, where the adapter of the invention then allows axial ballhead displacement on account of its cylindrical outer surface.

In summary, the present invention is an endoprosthesis for an artificial hip-joint comprising a shank, an adaptor at one end of the shank and a ballhead fitted with a recess engaged by the adaptor in a detachable manner and by the ballhead in a retaining manner and characterized in that the adapter and the recess are cylindrical and provided with means for retaining the ballhead in various axial positions relative to the adapter.

These and other objects of the present invention are elucidated below in relation to the detailed specification, representative embodiments and the drawings.

BRIEF DESCRIPTION OF THE DRAWINGS

FIG. 1 is a side elevational view of a first embodiment of the present invention having the ballhead shown in cross-section;

FIG. 2 is an enlarged side elevational view of a second embodiment of the present invention with portions of the shank shown broken away and also showing the ballhead in cross-section.

DETAILED DESCRIPTION OF THE PREFERRED EMBODIMENTS

Figure 3:
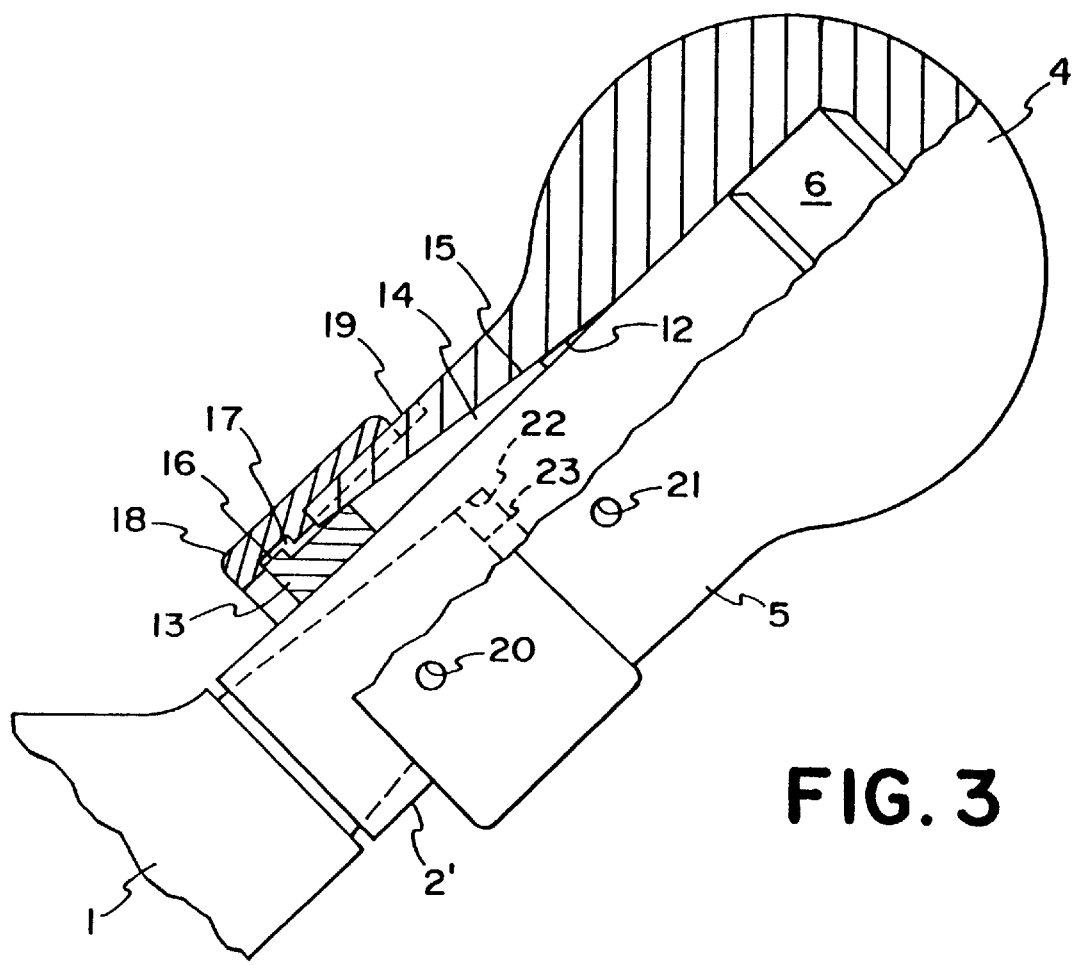
FIG. 3 is an alternative embodiment of the device shown in FIG. 2.

Turning to FIG. 1, an endoprosthesis according to the present invention is shown to comprise a shank 1 configured for insertion into a patients thighbone and being fitted with an adapter 2 having an outside thread 3. A cylindrical recess 6 having an inside thread 7 is present in a ballhead 4 and its extension 5.

A cross-borehole 8 is present in the extension 5, and cross-boreholes 9 are present in the cylindrical adapter 2 as well. In the position shown, the cross-borehole 8 in extension 5 is aligned with one of the cross-boreholes 9 in the cylindrical adapter 2, and, in that position, a securing pin 10 is force-fitted into the two said boreholes 8 and 9. The ballhead 4 is thereby secured against rotation when in the shown threaded-in position and also against axial displacements relative to the adapter 2.

FIG. 1 also shows the front edge 11 of the extension 5 is spaced from the cross-borehole 8 by about twice the spacing of the equidistant cross-boreholes 9 or a multiple thereof. Such configuration ensures that when the front edge 11 of the extension 5 is aligned with a cross-borehole 9 in the adapter 2, the cross-borehole 8 in the extension 5 also will be aligned with one of the cross-boreholes 9 and as a result, a securing pin 10 can be forced into its position. In this manner, the unnecessary search for the particular aligned positions becomes superfluous.

To install the device within a patient, the endoprosthesis is first inserted by its shank 1 into the appropriately prepared thighbone (not shown), the ballhead 4 (if so desired) already being screwed-on into a desired threaded-in position. Thereupon the ballhead 4 is rotated to adjust its desired position relative to the adapter 2 and hence to the shank 1 with such adjustment being possible only at those steps wherein the cross-borehole 8 is aligned with one of the cross-boreholes 9. This aligned position can be ensured by checking to see that the front edge 11 is flush with one of the cross-boreholes 9.

FIG. 2 shows a second embodiment of the invention and substantially corresponds to the upper portion of the device shown in FIG. 1, the same components being denoted by the same references. FIG. 2 is an enlarged view of the device with the ballhead 4 together with its extension 5 and the remaining elements, yet to be discussed, shown in half section.

In FIG. 2, the surface of the adapter 2 and the inside surface of the cylindrical recess 6 are shown to be smooth. Consequently the ballhead 4 can be displaced per se axially on the adapter 2.

In the region of the extension 5, the cylindrical recess merges into a conical recess 12 entered by a clamping sleeve 13 having a slitted conical end, the conical end 14 being fitted with an outside surface 15 that is complementary to the inside surface of the conical recess 12.

The clamping sleeve 13 comprises a radial, external collar 16 geometrically engaging an inside channel 17 of a coupling nut 18 screwed onto an outside thread 19 of the extension 5. Accordingly, the clamping sleeve 13 is geometrically locked-in to the coupling nut 18 regarding axial displacements while also being linked to it in a rotationally displaceable manner.

To tighten the coupling nut 18, the clamping sleeve 13 is pressed by its slitted conical end 14 into the conical recess 12 and thereby wedges the cylindrical adapter 2 against the extension 5. As a result, the ballhead 4 is firmly connected in its particular axial position to the adapter 2 by a clamp comprising, for example, sleeve 13 and nut 18.

This connection may readily be undone by loosening of the coupling nut 18 which in turn pulls the clamping sleeve 13 out of the wedged position by means of collar 16.

A blind hole 20 for receiving a pin wrench is present in the coupling nut 18 to permit tightening and loosening. To accommodate the reaction force, an appropriate pin wrench may be inserted into a blind hole 21 in the extension 5.

FIG. 3 shows a further embodiment of the device shown in FIG. 2. The same components are denoted by the same references in both figures. The essence of the variation is that the adapter 2' constitutes a separate part comprising a recess 22 at its end facing the shank 1, the recess 22 being conically complementary to a conical adapter 23 mounted at one end of the shank 1. Accordingly, the adapter 2' is self-locking when placed on the conical adapter 23, the cone angle obviously requiring commensurate selection known to any expert.

As regards the embodiment mode of FIG. 3, the shank 1 with the conical adapter 23 may evince the conventional design. By placing the adapter 2' on this known shank, a design is then achieved which allows application of the principle of the invention; namely, the ability to adjust the ballhead 4 in the axial direction of the adapter 2'.

I claim:

1. An adjustable endoprosthesis for an artificial hip joint comprising:
    a) a shank having a first end and a second end;
    b) a substantially cylindrical adapter coextensive with one of said first and second ends;
    c) a ballhead including a ballhead extension, said ballhead and said extension provided with a substantially cylindrical coextensive recess engagible to said adapter in a plurality of axial positions along the longitudinal axis thereof;
    d) a fastener operatively associated with each of said adapter and said ballhead whereby said ballhead may be fixed to said adapter in a selected axial position relative to said adapter; and
    e) said fastener is a clamp.

2. An endoprosthesis for an artificial hip joint as in claim 1 and wherein:
    a) said clamp is a clamping sleeve.

3. An endoprosthesis for an artificial hip joint as in claim 2 and wherein:
    a) said clamping sleeve having a cylindrical inside surface and is axially displaceable on said adapter whereby a first end of said clamping sleeve comprises a conically tapering outside surface that is received into a complementary conical portion of said recess inside said ballhead, a second other end of said clamping sleeve rests against a fastener secured to said ballhead.

4. An endoprosthesis for an artificial hip joint as in claim 3 and wherein:
    a) said clamping sleeve is axially slitted at least in said conically tapering outside surface.

5. An endoprosthesis for an artificial hip joint as in claim 2 and wherein:
    a) said fastener further including a coupling nut screwed onto Said ballhead extension.

6. An endoprosthesis for an artificial hip joint as in claim 5 and wherein:
    a) said coupling nut extends in the same direction as said clamping sleeve and is movable therewith.

7. An endoprosthesis for an artificial hip joint as in claim 2 and further comprising:
    a) at least one cross-borehole in the form of a blind hole provided in an outside surface of said extension of said ballhead for receiving a pin wrench.

8. An endoprosthesis for an artificial hip joint as in claim 6 and further comprising:
    a) at least one cross-borehole in the form of a blind hole provided in an outside surface of said extension of said coupling nut for receiving a pin wrench.

9. An endoprosthesis for an artificial hip joint as in claim 1 and wherein:
    a) said adapter is a separate member and includes a recess for interfit with a first end facing said shank, said recess is conically complementary to a conical adapter provided at said first end of said shank and in a manner such that said adapter is mountable in a self-locking manner to said conical adapter.

* * * * *